(12) United States Patent
Hogan

(10) Patent No.: US 10,820,840 B2
(45) Date of Patent: Nov. 3, 2020

(54) OPTICAL COHERENCE TOMOGRAPHY FOR IDENTITY VERIFICATION

(71) Applicant: Joshua Noel Hogan, Los Altos, CA (US)

(72) Inventor: Joshua Noel Hogan, Los Altos, CA (US)

(*) Notice: Subject to any disclaimer, the term of this patent is extended or adjusted under 35 U.S.C. 154(b) by 17 days.

(21) Appl. No.: 16/091,462

(22) PCT Filed: Apr. 4, 2017

(86) PCT No.: PCT/US2017/029716
§ 371 (c)(1),
(2) Date: Oct. 4, 2018

(87) PCT Pub. No.: WO2017/189775
PCT Pub. Date: Nov. 2, 2017

(65) Prior Publication Data
US 2019/0150799 A1 May 23, 2019

Related U.S. Application Data

(60) Provisional application No. 62/360,422, filed on Jul. 10, 2016, provisional application No. 62/328,804, filed on Apr. 28, 2016.

(51) Int. Cl.
*A61B 5/1171* (2016.01)
*A61B 3/18* (2006.01)
(Continued)

(52) U.S. Cl.
CPC ............ *A61B 5/1171* (2016.02); *A61B 3/102* (2013.01); *A61B 3/112* (2013.01); *A61B 3/18* (2013.01);
(Continued)

(58) Field of Classification Search
None
See application file for complete search history.

(56) References Cited

U.S. PATENT DOCUMENTS 8,509,495 B2 * 8/2013 Xu .................... G06K 9/00013
235/380
8,553,948 B2 * 10/2013 Hanna ................ G06K 9/00604
382/117

(Continued)

FOREIGN PATENT DOCUMENTS

CN 201310355600 * 8/2013

OTHER PUBLICATIONS

A. Czajka, ",Pupil Dynamics for Iris Liveness Detection" in IEEE Transactions on Information Forensics and Security, vol. 10, No. 4, pp. 726-735, Apr. 2015. (Year: 2015).*

(Continued)

*Primary Examiner* — Andrae S Allison

(57) ABSTRACT

A system and method for using optical coherence tomography for identity authentication. Embodiments include fingerprint validation, iris scan validation and facial scan validation. A preferred embodiment uses an optical coherence tomography system in conjunction with at least one additional two or three dimensional imaging of fingerprint, iris or facial biological indicators. Various embodiments provide additional combinations of two and three dimensional identification features so as to increase likelihood of accurate authentication of a subject under test.

8 Claims, 13 Drawing Sheets

(51) Int. Cl.
*G06K 9/00* (2006.01)
*A61B 5/117* (2016.01)
*A61B 5/00* (2006.01)
*A61B 3/10* (2006.01)
*A61B 3/11* (2006.01)
*A61B 5/026* (2006.01)
*A61B 5/1172* (2016.01)

(52) U.S. Cl.
CPC .......... *A61B 5/0066* (2013.01); *A61B 5/0261* (2013.01); *A61B 5/117* (2013.01); *G06K 9/00597* (2013.01); *G06K 9/00604* (2013.01); *G06K 9/00892* (2013.01); *G06K 9/00899* (2013.01); *G06K 9/00906* (2013.01); *A61B 5/1172* (2013.01); *A61B 5/1176* (2013.01); *A61B 2576/02* (2013.01); *G06K 9/00006* (2013.01); *G06K 9/00221* (2013.01); *G06K 2009/00932* (2013.01); *G06K 2009/00939* (2013.01)

(56) References Cited

U.S. PATENT DOCUMENTS

| 8,687,856 | B2* | 4/2014 | Bower | G06K 9/00006 348/78 |
| 8,718,335 | B2* | 5/2014 | Mason | G06K 9/00604 382/117 |
| 8,870,376 | B2* | 10/2014 | Hogan | A61B 3/14 351/206 |
| 9,808,154 | B2* | 11/2017 | Cleland | A61B 3/1233 |
| 10,380,418 | B2* | 8/2019 | Agrawal | G06K 9/4604 |
| 2008/0278683 | A1* | 11/2008 | Su | G01J 9/00 351/205 |
| 2011/0150293 | A1* | 6/2011 | Bower | G06K 9/00006 382/117 |
| 2013/0010259 | A1* | 1/2013 | Carnevale | A61B 3/102 351/206 |
| 2015/0178547 | A1* | 6/2015 | Bahjat | G06K 9/0061 382/117 |
| 2015/0363630 | A1* | 12/2015 | Hogan | G06K 9/0002 356/479 |
| 2016/0038021 | A1* | 2/2016 | Bagherinia | G01B 9/02083 351/246 |
| 2017/0124408 | A1* | 5/2017 | Hogan | G06K 9/00046 |

OTHER PUBLICATIONS

Y. Chen and W. Zhang, "Iris Liveness Detection: A Survey," 2018 IEEE Fourth International Conference on Multimedia Big Data (BigMM), Xi'an, 2018, pp. 1-7. (Year: 2018).*

A. Lagorio, M. Tistarelli, M. Cadoni, C. Fookes and S. Sridharan, "Liveness detection based on 3D face shape analysis," 2013 International Workshop on Biometrics and Forensics (IWBF), Lisbon, 2013, pp. 1-4. (Year: 2013).*

J. Galbally, J. Ortiz-Lopez, J. Fierrez and J. Ortega-Garcia, "Iris liveness detection based on quality related features," 2012 5th IAPR International Conference on Biometrics (ICB), New Delhi, 2012, pp. 271-276. (Year: 2012).*

* cited by examiner

Fig. 8A Side image of iris

Fig. 8B Front image of iris

OPTICAL COHERENCE TOMOGRAPHY FOR IDENTITY VERIFICATION

CROSS REFERENCES TO RELATED PATENTS OR APPLICATIONS

This utility patent application claims priority from U.S. provisional application 62/328,804 filed Apr. 28, 2016, the entirety of which is incorporated by reference as if fully set forth herein. This application is also related to U.S. provisional patent application, 62/360,422 also titled "Method and system for verifying bio authenticity" filed Jul. 10, 2016, the entirety of which is incorporated by reference as if fully set forth herein. This application is also related to U.S. patent application Ser. No. 14/738,919 titled "System and Method for Fingerprint Validation" filed on Jun. 14, 2015 and to provisional patent application 62/197,079 titled "A method and system for verifying document authenticity" filed on Jul. 26, 2015, the contents of both of which are incorporated by reference herein as if fully set forth herein. This invention is also related to U.S. Pat. No. 7,526,329 titled Multiple reference non-invasive analysis system and U.S. Pat. No. 7,751,862 titled Frequency resolved imaging system, the contents of both of which are incorporated by reference herein as if fully set forth.

GOVERNMENT FUNDING

None.

FIELD OF USE

The invention relates to non-invasive imaging and analysis techniques such as Optical Coherence Tomography (often referred to herein as "OCT"). In particular it relates to using optical interferometric techniques to monitor or measure sub-surface attributes of living tissue. It also relates to correlating changes in such attributes with a response to at least one stimulus, where a stimulus can be generated within the living tissue or externally generated. Such a stimulus is, typically, physical or psychological. Resulting information about the response to a stimulus can be used in bio-security applications to determine that the tissue being monitored or analyzed is real living tissue. Resulting information about the response to a stimulus can also be used in bio-medical applications to evaluate medical aspects of the living tissue of the subject being monitored or analyzed.

BACKGROUND

Bio-security techniques, such as fingerprint and iris recognition typically analyze surface features to determine identity and are therefore vulnerable to presentation of an artificial or fake fingerprint or fake iris also referred to as a "spoof" Involuntary reaction to an external stimulus is the basis of several bio-security and bio-medical techniques. For example, in lie detection techniques for bio-security applications, aspects of human skin, such as skin conductivity are measured to determine truthfulness of answers to questions based on changes is such measured aspects. In fingerprint identification, aliveness detection techniques, such as detection of the presence of blood flow, are used as anti-spoof techniques. See, for example, S. CHANG, et al Optical coherence tomography used for security and fingerprint-sensing applications, IET Image Process., 2008, Vol 2, No. 1, pp 48-58.

Non-invasive imaging and analysis of targets using optical coherence tomography (OCT) is a powerful technique for acquiring sub-surface information without damaging the target or system being analyzed. The ability of OCT to analyze or monitor structures within tissue, or dynamic aspects of tissue, enables adding a security layer to conventional bio-metric systems, such as fingerprints or iris recognition, by correlating the conventionally observable information with sub-surface information acquired by the OCT system.

Multiple Reference OCT (MRO) is a version of TD-OCT that uses multiple reference signals. Another OCT technique is Fourier Domain OCT (FD-OCT). A version of Fourier Domain OCT, called Swept Source OCT (SS-OCT), typically uses a narrow band laser optical source whose frequency (or wavelength) is swept (or varied) over a broad wavelength range. In TD-OCT systems the bandwidth of the broadband optical source determines the depth resolution. In SS-OCT systems the wavelength range over which the optical source is swept determines the depth resolution.

Another version of Fourier Domain OCT, often referred to as Spectral Domain OCT (SD-OCT), typically uses a broad band optical source and uses a spectrometer to separate out wavelengths and detect signals at different wavelengths by means of a multi-segment detector.

OCT depth scans can provide useful sub-surface information including, but not limited to: sub-surface images of regions of tissue; measurement of thickness of layers of tissue; magnitude of regions of abnormal tissue growth; measurement of concentration of metabolites, such as glucose, in tissue fluids; measurement of concentration of metabolites, such as glucose, in blood. More generally OCT depth scans can provide useful sub-surface information regarding attributes of tissue.

While conventional fingerprint sensors, such as an array of capacitive sensors or an array of conducting sensors or arrays of pressure or ultrasound sensors, optionally in conjunction with an RF generator, are used to ensure use by authorized individuals, such sensors are vulnerable to being hacked, for example, by artificial (stick on) fingerprints.

Similarly conventional iris recognition techniques are vulnerable to being hacked by the use of a contact lens based false iris or by an iris implant. Furthermore simply monitoring a change in pupil size with light level as a technique for detecting a false iris is vulnerable to being hacked, for example, by inclusion of concentric rings of light sensitive absorption material in a false (or fake) iris or eye.

There is therefore an unmet need for a more secure identification and authentication technique. What is needed is a system and method for validating that the conventional identification techniques, such as fingerprint and iris recognition, that is augmented by correlating the conventionally measured information, including dynamic information, with additional three dimensional or sub-surface information.

BRIEF DESCRIPTION OF THE INVENTION

The invention meets at least all of the aforementioned unmet needs.

The invention provides an improved, secure identification and authentication technique. The invention provides a system and method for validating or augmenting conventional identification techniques, such as fingerprint and iris recognition, by correlating the conventionally measured information, including dynamic information, with additional three dimensional or sub-surface information.

A number of embodiments are described herein.

In one embodiment, the inventive system provides a conventional camera imaging the iris and an OCT system acquiring a three dimensional and sub-surface image of the iris, and an optional second conventional camera. The acronym OCT as used herein means Optical Coherence Tomography.

A system for analyzing an iris in an eye under test comprising: an optical coherence tomography system, including a processing system; a first conventional camera; wherein said first conventional camera monitors dynamic behavior of the pupil of said iris with respect to changing light levels and wherein said optical coherence tomography system monitors dynamic behavior of preselected sub-surface components of said iris under test with respect to changing light levels, and wherein a processing system analyzes dynamic behavior of said pupil and said subsurface components so as to determine the correspondence of the conventional camera data and the sub-surface component data and thereby determine the authenticity of said iris under test.

In one embodiment, the sub-surface component of interest is a sphincter muscle of the pupil of said iris, and authenticity is determined by verification of contraction of said sphincter muscle as a consequence of increase in light illumination on said eye. Authenticity is also determined by verification of the identity of the subject by comparing aspects of the iris image, obtained by the conventional camera, with previously stored iris data relating to the same subject.

Conventional biometric imaging and measuring technologies are augmented by the use of an OCT system to non-invasively acquire three dimensional and sub-surface information which is then correlated with the conventionally acquired image and measurement information to (a) verify that the three dimensional and sub-surface information is compatible with real tissue (b) where relevant, verify that the three dimensional and sub-surface information correlates with the conventionally acquired information (c) where relevant, verify that dynamic changes in the three dimensional and sub-surface information correlate with changes in the conventionally acquired information and (d) where relevant, verify that dynamic changes in the three dimensional and sub-surface information correlate with changes in the conventionally acquired information where such changes are in response to a stimulus.

Such a stimulus can be a routine internal stimulus, such as heartbeat or pulse rate, or an external stimulus. An external stimulus can be physical, such as a mild electric shock, or a change in light level. Alternatively or additionally, an external stimulus can be psychological, such as stressful questioning.

In the case of iris recognition, the recognition system can be made more robust by augmenting conventional iris recognition by the use of an OCT system to: (a) detect the presence of an external false iris, such as a contact lens, by monitoring for the sub-surface interface between the back of the contact lens and the front of the cornea and detecting if there is a front surface of the contact lens; (b) detect an iris implant by monitoring the three dimensional structure of the iris and correlating such structure with the conventional 2D iris image; (c) detect the presence of blood in the iris; (d) detect blood flow in the iris; (e) detect blood flow rate in the iris and correlate it with pulse rate; (f) detect and correlate change in blood flow with response to a stimulus; (g) detect and correlate dynamic change sub-surface iris tissue components with dynamic change in pupil diameter with response to a stimulus, such as a change in light level.

The OCT system also detects an iris implant by (a) imaging the three dimensional structure of the iris, for example, to verify presence of the thin posterior epithelium on the rear surface of the iris and to verify that it conforms to the typical layered structure; (b) detecting the presence of the sphincter muscle located by the pupil; (c) detect the change in shape of a sphincter muscle, or the change in shape of other iris structures, as light intensity is varied; and (d) correlate the change in shape of a muscle or other tissue structure or component as light intensity is varied with the change in pupil diameter in response to a light intensity variation.

In the case of fingerprint recognition, (a) aspects of the sub-dermal structure of tissue under the conventional fingerprint are monitored to verify that it is real living tissue (as opposed to a fake fingerprint) (b) aspects of the sub-dermal fingerprint are correlated with the surface fingerprint to verify that the sub-dermal is consistent with the surface fingerprint (as described in the patent application incorporated herein by reference), (c) physical variation in the size of blood vessels or the speed of blood flow is monitored by the OCT system and correlated with the pulse rate as monitored by conventional pulse rate or heart beat monitors. Furthermore, changes in the physical variation in the size of blood vessels or the speed of blood flow is correlated with changes in the pulse rate or heart beat rate due to an external stimulus, where such a stimulus can be physical or psychological, (d) compression of tissue is monitored by, for example, my measuring the epidermis thickness or the thickness of other layers, and changes in the measured compression are correlated with the changes in the pressure with which the finger applied to the fingerprint platen, where such changes in pressure can be due to the application or removal of the finger from the platen or where an additional sensor monitors the actual pressure of the finger on the platen.

In the case of facial recognition, sub-surface scanning of the surface of the face by the OCT system can be used to verify that the facial tissue has a typical tissue layer structure and is not covered by a mask, for example a liquid latex mask or other disguising make-up. The OCT system can also be used to: detect the presence of blood; blood flow, that the measured blood flow rate varies corresponding with the pulse rate; that a change in blood flow intensity is accompanied by a corresponding change in facial color and/or temperature due, for example, to blushing or blanching in response to stressful questions or stimuli.

OCT measurements acquired by multiple OCT systems or a single OCT system are used to perform multiple measurements. For example an OCT system housed in a goggle like face mounted device makes iris measurements and the OCT beam is routed to make facial measurements. Facial measurements include, for example, monitoring blood flow in the nose.

Other embodiments of a more secure identification and authentication technique include measuring (a) the presence and thickness of a tear film (b) the profile of the tear meniscus at an eye lid margin, referred to as "the tear lake" (c) other parameters of eye including, but not limited to, corneal thickness and curvature, lens thickness, axial length of the eye, (d) mechanical parameters of tissue e.g. how skin deforms and relaxes in response to pressure (e) the polarization changes to light scattered by tissue, for example to determine that linearly polarized light is depolarized and exhibits the birefringence of real tissue or that circularly polarized light exhibits the birefringence of real tissue, (f) the 3D structure of the front of the iris.

Secure identification is expedited by targeted small OCT three dimensional (or volume) scans of specific areas of tissue. For example, in the fingerprint case information related to the identification and location of minutiae is determined from the surface fingerprint and this information is used to direct the OCT scanning system to scan specific small volumes that include at least portions of at least some of the minutiae.

Information related to the identification and location of minutiae of the surface fingerprint is also used to target tissue volumes including sweat glands. Variation in the intensity of light scattered from one or more sweat glands is monitored as a verbal (or other) stimulus is applied. Such verbal stimuli include, but are not limited to, questions related to an individual's identity, background, or history.

In the case of iris scanning, targeted OCT scanning uses iris surface topography to locate the OCT scanning system, for example to scan a volume that includes a sphincter muscle or other sub-surface iris component that varies in response to a light level stimulus designed to dilate or contract the pupil.

A method according to one embodiment of the invention comprises the steps of: selecting at least two biological indicators, exposing subject under test to at least one pre-selected dynamically changing stimulus; monitoring said at least two biological indicators; processing data obtained during dynamically changing stimulus, and determining whether biological indicators satisfy authenticity criteria. In a preferred embodiment relative to iris recognition, indicators are selected dynamic indicators, including change in pupil diameter and change in sphincter muscle shape. In facial recognition selected dynamic indicators in a preferred embodiment are blood flow increase or decrease. In fingerprint analysis, selected dynamic indicators are a first and a second pulse blood flow. In alternate embodiments, two and three dimensional imaging approaches include ultrasound, surface profilometry, video camera, and video camera in combination with structured lighting.

It should be understood that the above description is illustrative and not restrictive. Numerous modifications and variations could be made thereto by those skilled in the art without departing from the spirit and scope of the invention. It is therefore to be understood that the invention may be practiced otherwise than as specifically described herein.

BRIEF DESCRIPTION OF THE DRAWINGS

The drawings provided as an aid to understanding the invention.

DETAILED DESCRIPTION OF A PREFERRED EMBODIMENT

Figure 1:
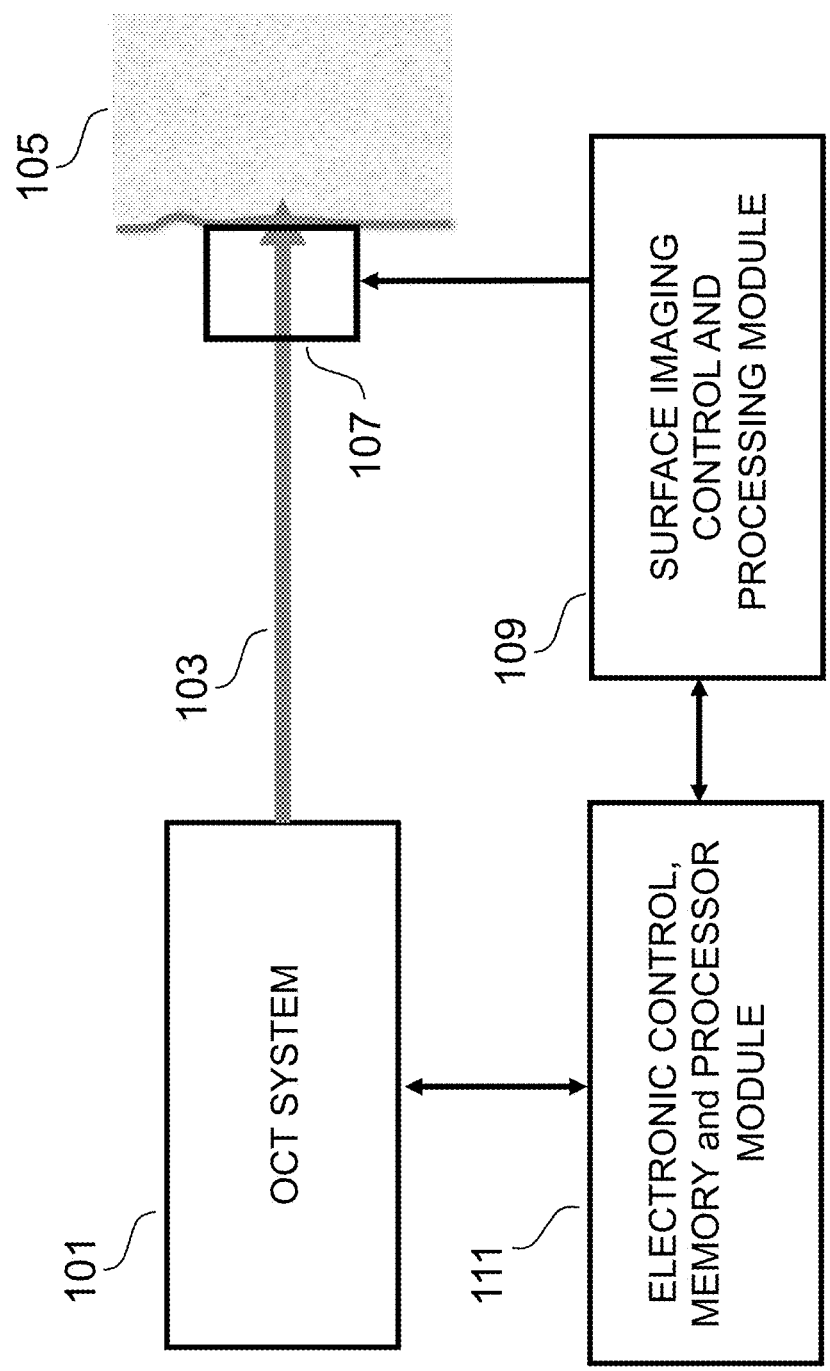
FIG. 1 is an illustration of a system according to the invention.

Terminology and abbreviations used herein. Applicant intends the commonly understood meaning of terms herein. A selection of terms used in this specification and the intended meanings are set forth herein below as an aid to understanding the invention.

Authentication: as used herein means verifying subject identity and aliveness of subject, as in, for example, bio-authenticity.

B-scan: a cross sectional tomographic scan obtained using optical coherence tomography;
 a scan that includes a sub-surface scan.
 CCD: Charge Couple Device
 CMUT: capacitive micro-machined ultrasonic transducer
 Conventional fingerprint: a surface fingerprint; an image of the surface of the skin—the outer epidermis—on a fingertip; any fingerprint image obtained other than by the inventive method and system. Conventional image (and conventional imaging system) includes an image obtained by a camera, a photocopy, or any other common imaging techniques for imaging the surface fingerprint or tissue layer in a two dimensional representation.
 OCT: Optical Coherence Tomography
 Primary fingerprint: a term used in the field of fingerprint analysis, referring to the region where the epidermis and the dermis meet. Alternately termed "sub-surface fingerprint"; "sub-dermal fingerprint"
 Registration: the alignment of the cross sectional tomographic scan with the conventional fingerprint. In a system according to the invention, registration is ensured by the physical arrangement of the optical coherence tomography system and the surface imaging system or device. The position of the OCT is calibrated with respect to the imaging system. Such calibration using, for example, a test pattern, is understood by those of average skill in the relevant art and needs no further elaboration. Calibration includes alignment at multiple surface positions.
 Stimulus: an physical event such as; a change in light level, change in pressure; change in temperature; application of a weak electric voltage or current; or a psychological event such as questioning in an unexpected, deceitful or aggressive manner.
 Sub-surface: below the surface of the target; below tissue outermost layer; area including tissue beneath the outermost tissue layer; The sub-surface fingerprint, also referred to as a sub-dermal fingerprint or as the primary fingerprint, is located at the interface of the epidermis and the dermis. In an individual's finger, the pattern in outermost layer of the epidermis matches the pattern at the interface of the epidermis and the dermis. Thus, the conventional surface fingerprint is a precise match, or, "copy" of this sub-dermal primary fingerprint.

Validating: in the case of an iris, determining that the three dimensional structure of the surface matches the conventional camera image, or that structures such as the thin posterior epithelium on the rear surface of the iris are present have typical characteristics; in the case of a fingerprint, determining that the target matches at the surface and at the interface of the dermis and the epidermis; validating also includes, in an alternate embodiment, determining blood flow, hence ensuring "aliveness". The processor outputs validation status.

Validation status: if positive validation, the output of status enables secure access. If validation fails, output of validation failure is used, for example, to decline device access.

A method useful in fingerprint validation comprises the steps of selecting a relative positioning of an optical coherence tomography system and a surface imaging device, with respect to each other; performing an optical coherence tomography scan to produce a cross sectional tomographic scan of said fingerprint, said scan including the interface of the epidermis and the dermis; obtaining a surface image of said fingerprint; validating said cross sectional tomographic scan using said surface image as a registration of said fingerprint and determining whether said cross sectional tomographic scan is compatible with the corresponding region of said surface image; outputting result of said validation step. Alternatively, the method further includes the step of obtaining a plurality of a cross sectional tomographic scans at substantially the same location, thereby enabling in less than one second, a determination of whether or not blood flow is present. In an alternate embodiment the step of performing optical coherence tomography scan includes using multiple reference optical coherence tomography.

Useful references, incorporated by reference as if fully set forth herein: A. ZAM, et al, Feasibility of correlation mapping optical coherence tomography (cmOCT) for anti-spoof sub-surface fingerprinting, Journal of Biophotonics, 25 Apr. 2013; ENFIELD, et al. "Correlation mapping method for generating microcirculation morphology from optical coherence tomography (OCT) intensity images," J. Biophotonics, 4(9), 583-587.

Also, published US applications appearing as publication numbers 2015/0363630, 2016/0174835, and 2016/0238370, incorporated by reference as if fully set forth herein.

Referring now to the Figures, an embodiment is depicted in FIG. 1 where the target is human tissue, and specifically the region referred to as "fingerprint", and where an OCT system 101 uses an optical beam 102 to non-invasively scan the target 105. A conventional imaging system 107 also captures a surface image of the target 105 which is processed by a surface image control and processing module 109.

An electronic control, memory and processor module 111 processes and stores an OCT scan of the tissue, acquired by the OCT system 101 in conjunction with the conventional surface image of the target. The physical relationship of the OCT system 101 and the conventional imaging system 107 are pre-selected, and is such that the OCT scans are at known or determined locations with respect to the conventional surface image of the target. Because the positions of the imaging system and the OCT probe beam with respect to each other are pre-selected so that the cross sectional tomographic scan is registered with the two dimensional surface image, it is possible to compare (or correlate) the structures shown in the B-scan with the precise corresponding features of the conventional image (i.e. ridges and valleys in the dermis-epidermis interface can be compared with ridges and valleys in the surface fingerprint). The processing module performs the correlations, and outputs validation that the fingerprint is a match or not.

The surface imaging system 107 is selected from one of the following or an equivalent: a CCD imaging system with an aperture through which the OCT probe beam can be applied to the target; an imaging system that is transparent at the wavelength of the OCT system; an ultra-sonic imaging array such as a capacitive micro-machined ultrasonic transducer (CMUT); an OCT imaging system, which may be the same OCT system that generates the sub-surface scans; a pressure sensitive array, such as is described in U.S. Pat. No. 7,795,062 titled "Method of forming a pressure switch thin film device".

Figure 2:
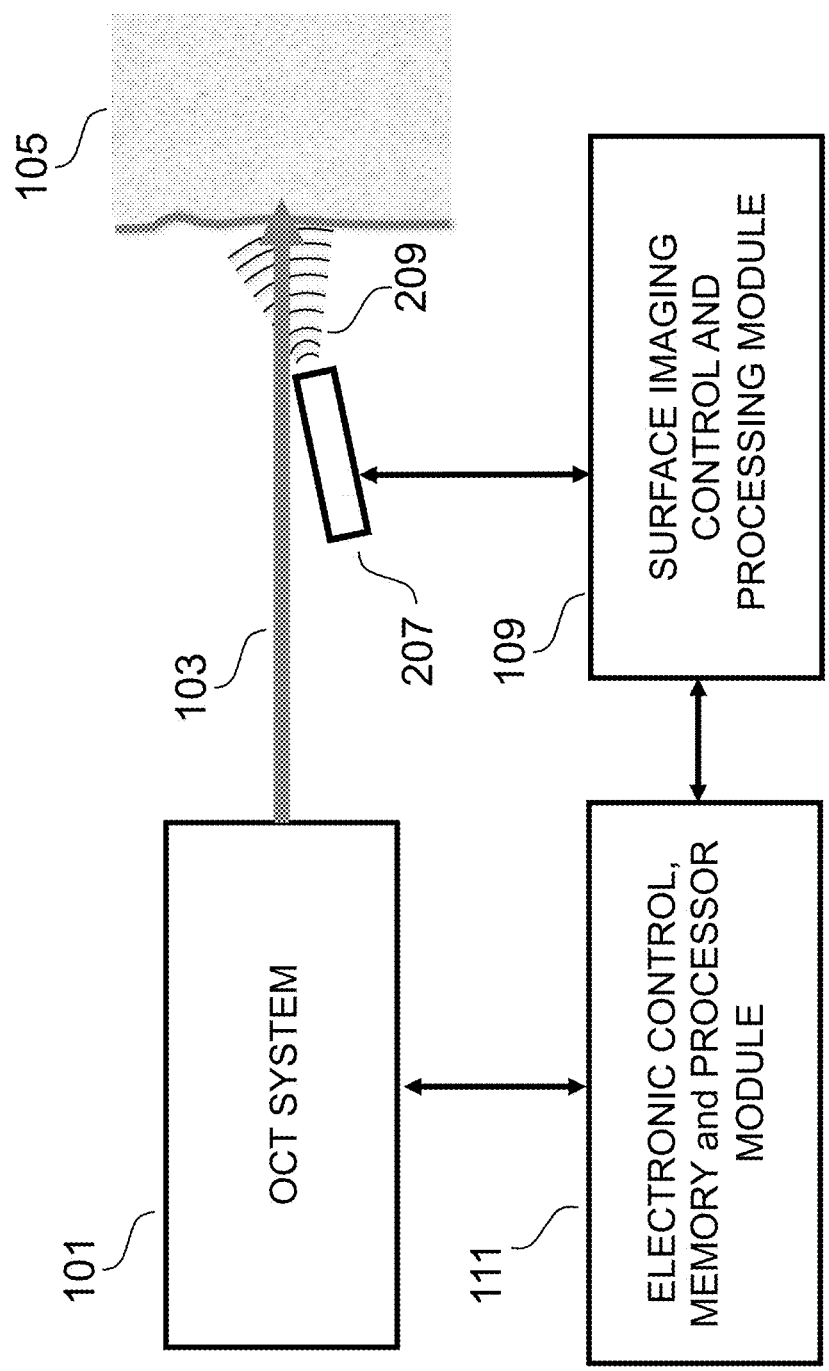
FIG. 2 depicts an alternate embodiment of a system according that invention.

FIG. 2 depicts an alternate embodiment. The surface imaging device 207 is offset from the path of the OCT probe beam. It can be appreciated that such an offset is necessary if the surface imaging device is not transparent. In an alternate embodiment, the surface imaging probe beam 209 is selected from a group of probe beam types, including an RF probe beam or an ultrasound probe beam.

Figure 3:
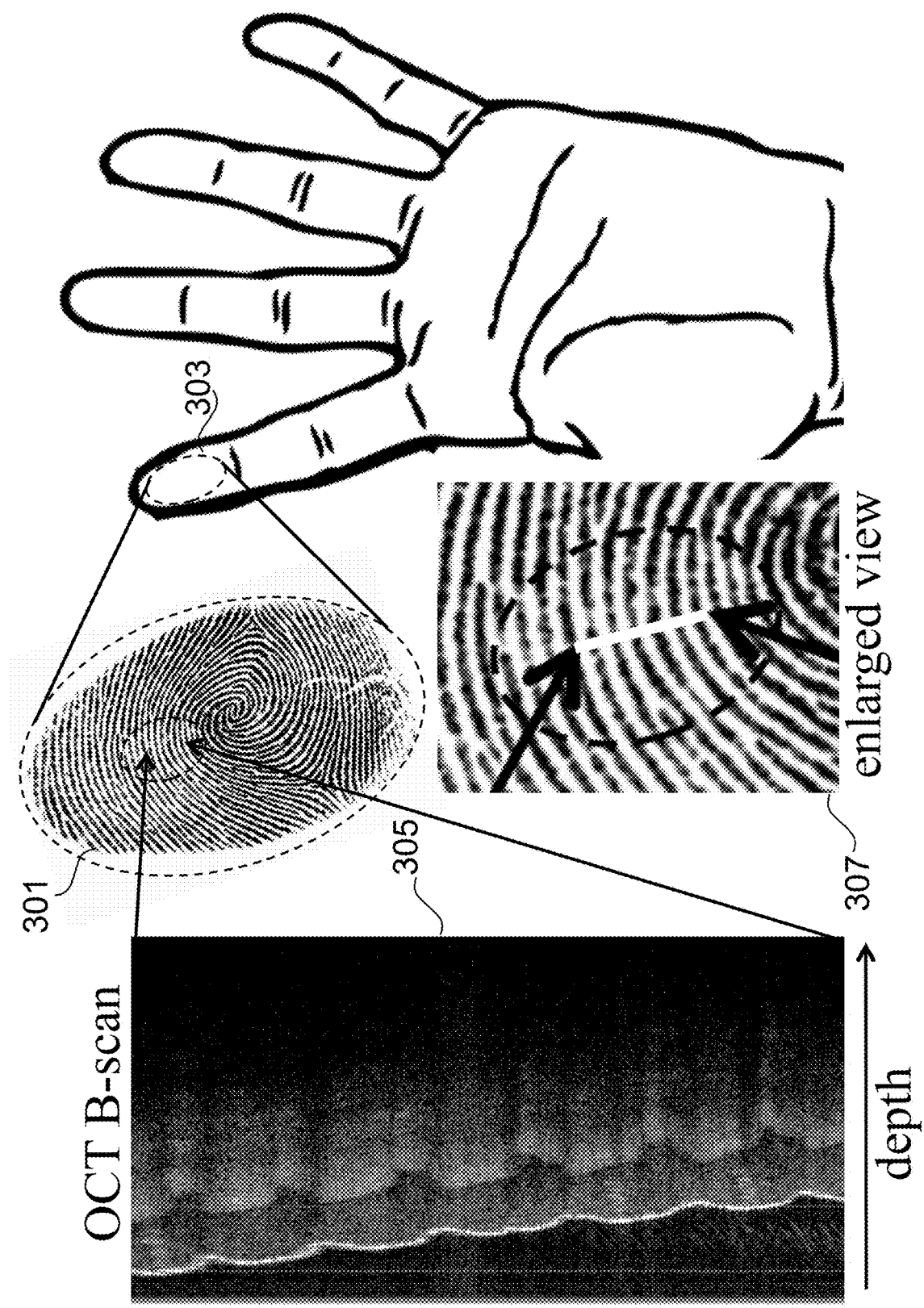
FIG. 3 depicts a cross section tomograph (a B-scan) together with a surface image, illustrating the application of that invention to human fingerprint verification.

FIG. 3 depicts a conventional surface fingerprint 301 of a typical human finger 303 and an OCT B-scan 305 of a region of the finger taken at a known location with respect to the surface image, indicated by the region between the two arrowheads inside the small oval. An enlarged view 307 more clearly depicts the small oval and the arrowheads that define the region of the OCT B-scan 305.

Figure 4:
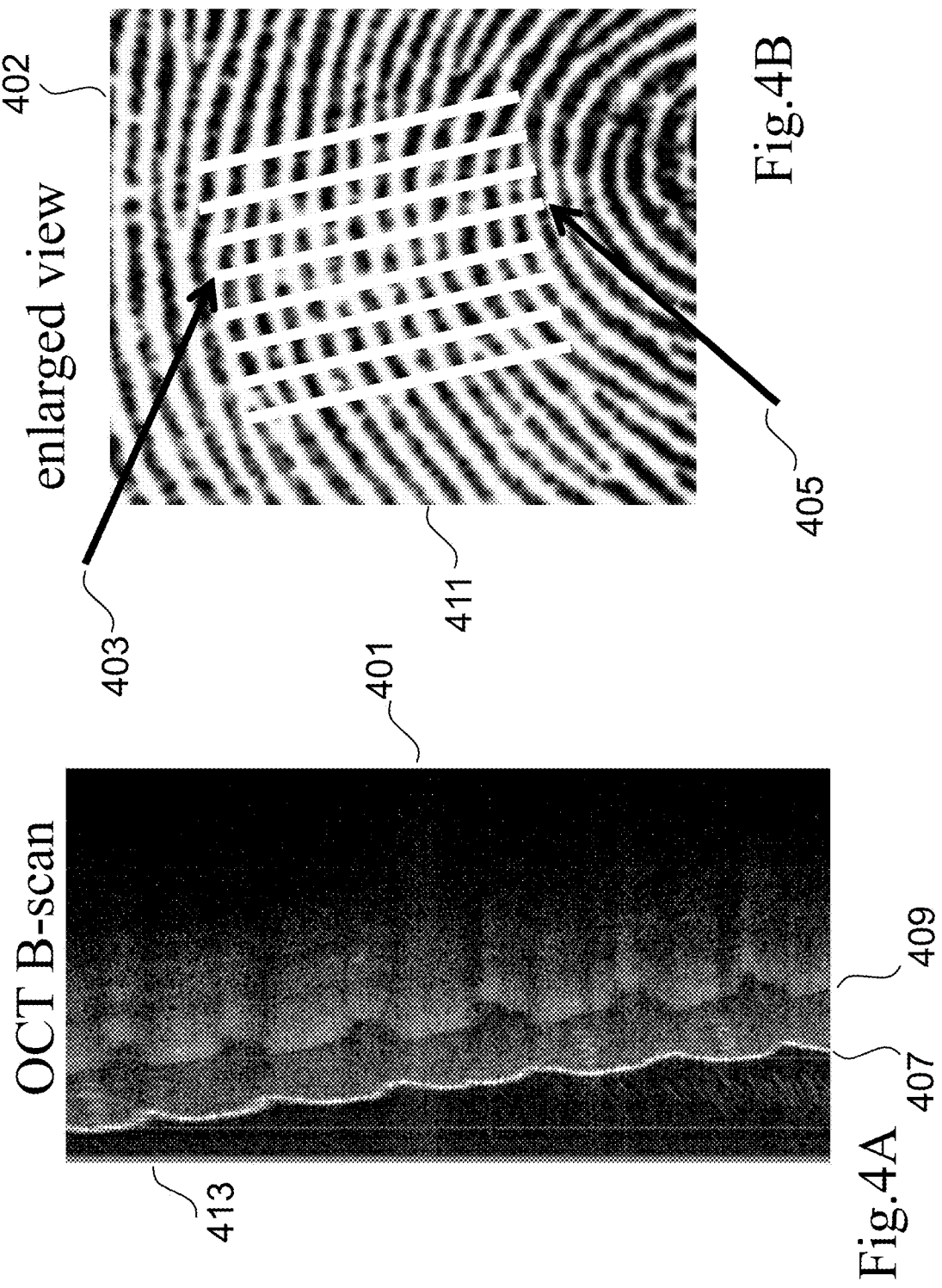
FIG. 4A shows a typical B-scan showing ridges and a surface fingerprint also showing ridges.
FIG. 4B.

In FIG. 4 the OCT B-scan 401 and the enlarged view 402 of the surface image are more clearly depicted. The arrows 403 and 405 indicate the region that corresponds to the cross sectional tomograph commonly referred to as an OCT B-scan 401. The OCT B-scan 401 includes a depiction 407 of the surface fingerprint image and also includes a depiction of a sub-surface version of the fingerprint 409, often referred to as a primary fingerprint. The sub-surface or primary fingerprint is generally understood to be the region where the epidermis and dermis meet.

The electronic control, memory and processor module 111 (of FIGS. 1 and 2) compares the sub-surface fingerprint image 409 with the portion of the B scan showing the surface (OCT image 407) and with the conventional fingerprint image 402 to validate that the sub-surface fingerprint is compatible with the corresponding region of a surface fingerprint.

In some embodiments, validation confirms that that the sub-surface (or primary) fingerprint 409 has contours that correspond to the contours of the surface fingerprint, i.e. that the sub-surface image and the surface image are appropriately compatible. For example the dark line 411 of the enlarged view of the surface image 402 corresponds to the OCT surface detail to the right of 413 and the deeper sub-surface (or primary) image farther to the right of 413 (along the contour of 409). The processing module outputs validation status. Validation status, for example, enables or prevents unlocking of a coupled electronic device such as, for example, a smart phone, a home security system, and other devices where secure access is desired. Note, the surface fingerprint image 402 is a typical example of and image and used herein for illustrative purposes.

While some embodiments describe an OCT B-scan 401 of FIG. 4 taken along a substantially straight line (between the arrow heads of 403 and 405 of FIG. 4) of a corresponding conventional fingerprint imaging device, many variations of the invention are possible. The OCT scan need not be a straight line. In an alternate embodiment, the OCT scan consists of an irregular line that is scanned with either a random or a particular relationship to features of the surface fingerprint.

In an alternate embodiment, the OCT performs a lateral scan consisting of a two-dimensional scan, such as, for example, a raster scan, providing a volumetric image. Such a volumetric image is compared to a surface image taken with a surface imaging device including, but not limited to, a CCD camera, an ultra sound imager, an RF imager, an array of pressure switches. Alternatively such a volumetric image is used to generate the surface image, thus removing the requirement for a separate surface imager.

Figure 5:
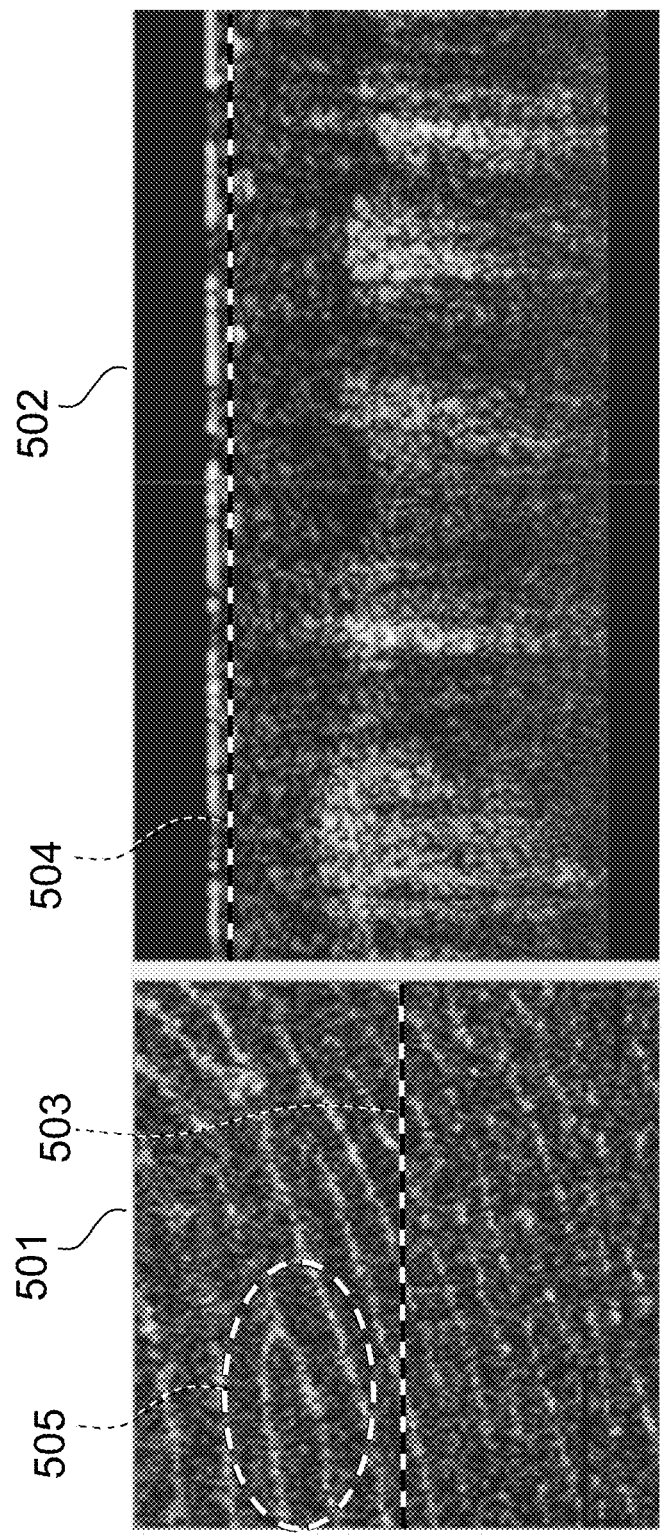
FIG. 5 shows a surface fingerprint and the corresponding B scan.

FIG. 5 illustrates a 2D image of a surface fingerprint 501 volumetric data generated by an OCT scanning system. FIG. 5 also depicts an OCT B-scan 502 which is a two dimensional depth image of the region of the 2D tissue image 501 indicated by the dashed line 503. The depicted 2D image of a surface fingerprint 501 is generated from OCT data just below the surface of a glass interface against which the finger was pressed and is indicated in the B-scan 502 as the dashed line 504. The dashed oval 505 surrounds a distinctive feature of the surface fingerprint.

Figure 6:
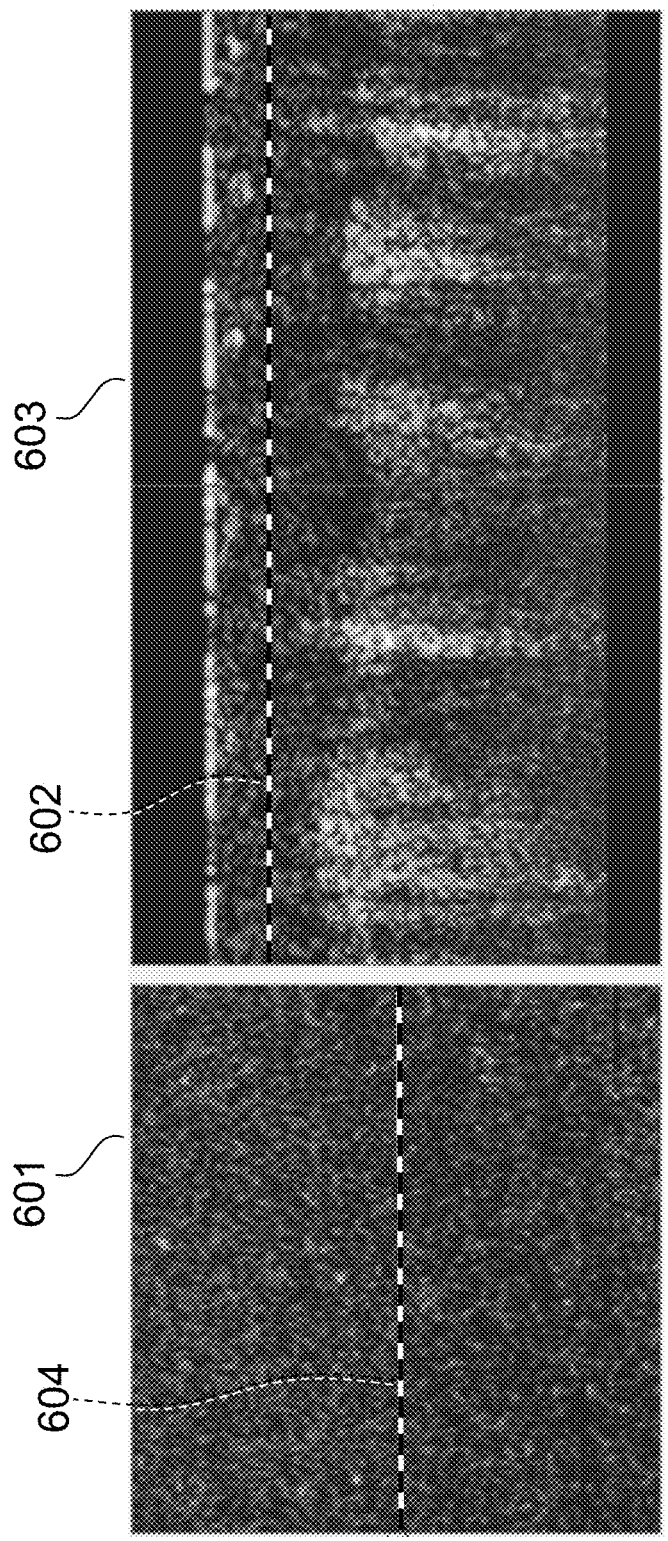
FIG. 6 shows a 2D (two dimensional) image below the surface, and a B scan, illustrating the absence of ridging pattern.

FIG. 6 illustrates a 2D image of a surface region 601 at a depth indicated by the dashed line 602 of the B-scan 603. This surface region 601 is at a depth beneath the surface fingerprint and above the epidermis dermis interface. The B-scan 603 is again located at the region indicated by the dashed line 604 of the 2D image 601. There is no similarity between this 2D image and the surface fingerprint image 501 of FIG. 5.

Figure 7:
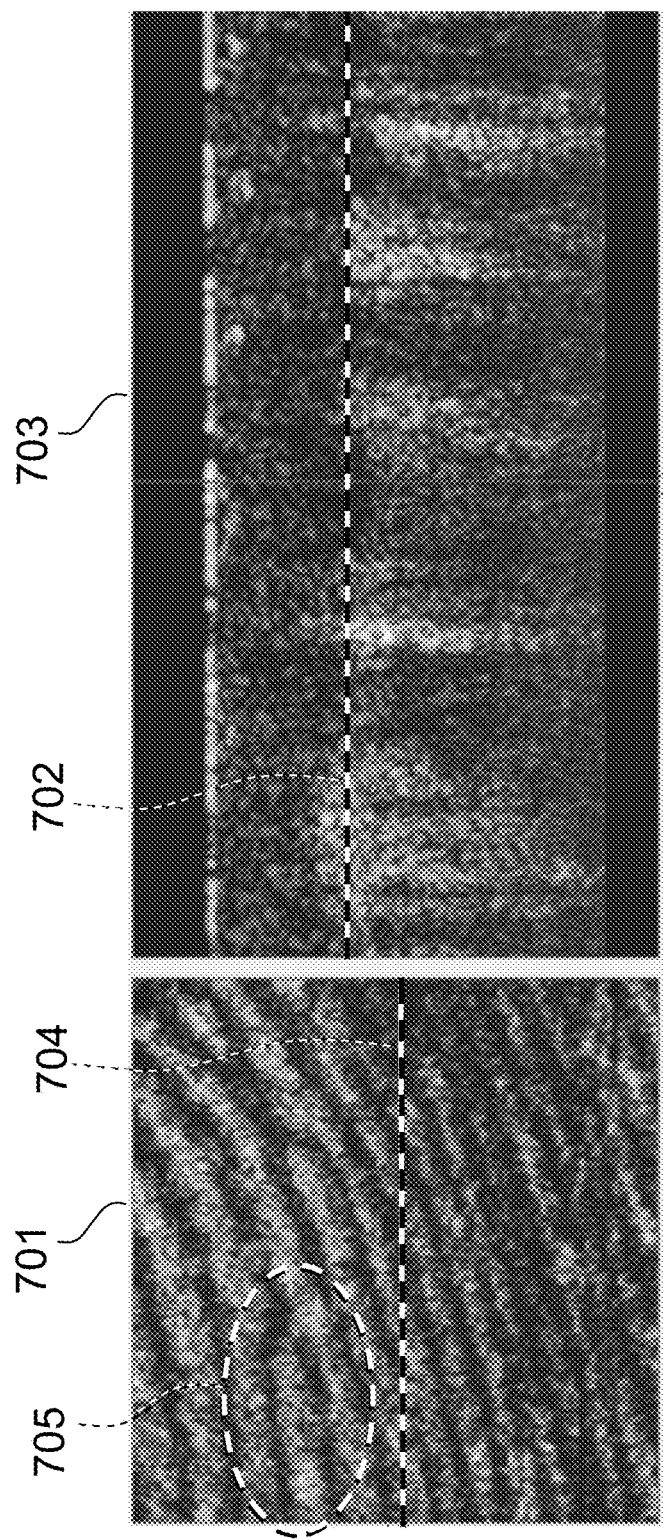
FIG. 7 shows a primary fingerprint, and a B-scan of the region where the epidermis and dermis meet, illustrating the matching ridges.

FIG. 7 illustrates a 2D image of a surface region 701 at a depth indicated by the dashed line 702 of the B-scan 703. This surface region 601 is at a depth in the region of the epidermis dermis interface. The B-scan 703 is again located at the region indicated by the dashed line 704 of the 2D image 701. This primary (sub-surface or sub-dermal) 2D fingerprint image 701 has a high degree of similarity with surface fingerprint image 501 of FIG. 5.

The similarity between the primary or sub-dermal 2D fingerprint image and the surface fingerprint image 501 of FIG. 5 is clearly evident in the regions depicted within the ovals 705 of FIG. 7 and 505 of FIG. 5. This high degree of similarity between the surface and sub-surface fingerprint images of an actual finger enables using conventional image processing techniques to measure the degree of correlation between two such images and to determine whether or not the images (and hence the surface and sub-surface fingerprints) correlate, i.e. to validate that the images are compatible with being different images of the same finger.

It can be appreciated that in an alternate embodiment, a random (or quasi-random) group of point scans are registered by means of the surface fingerprint and compared with extensive previously taken reference OCT data to validate correct tissue layer thickness at particular points. A further alternate embodiment provides an OCT system with multiple optical probe beams to acquire multiple OCT scans simultaneously.

In a system according to the invention, the OCT is selected from the group of any version of either Time Domain-OCT or Fourier Domain OCT systems, including the multiple reference version of Time Domain-OCT (described in some of the references incorporated herein).

Figure 8:
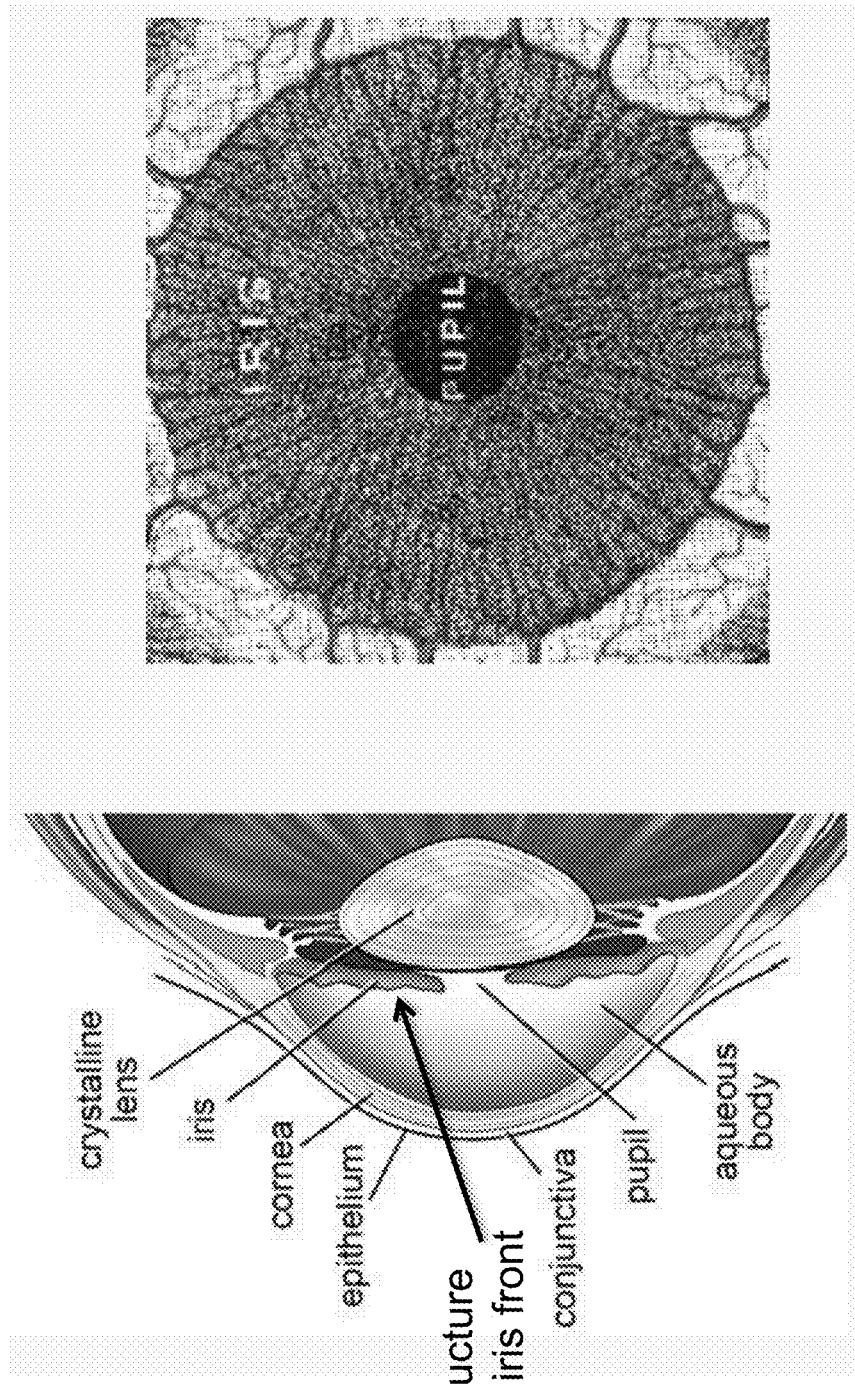
FIG. 8A depicts a side view of an iris.
FIG. 8B depicts a front view of an iris.
Figure 9:
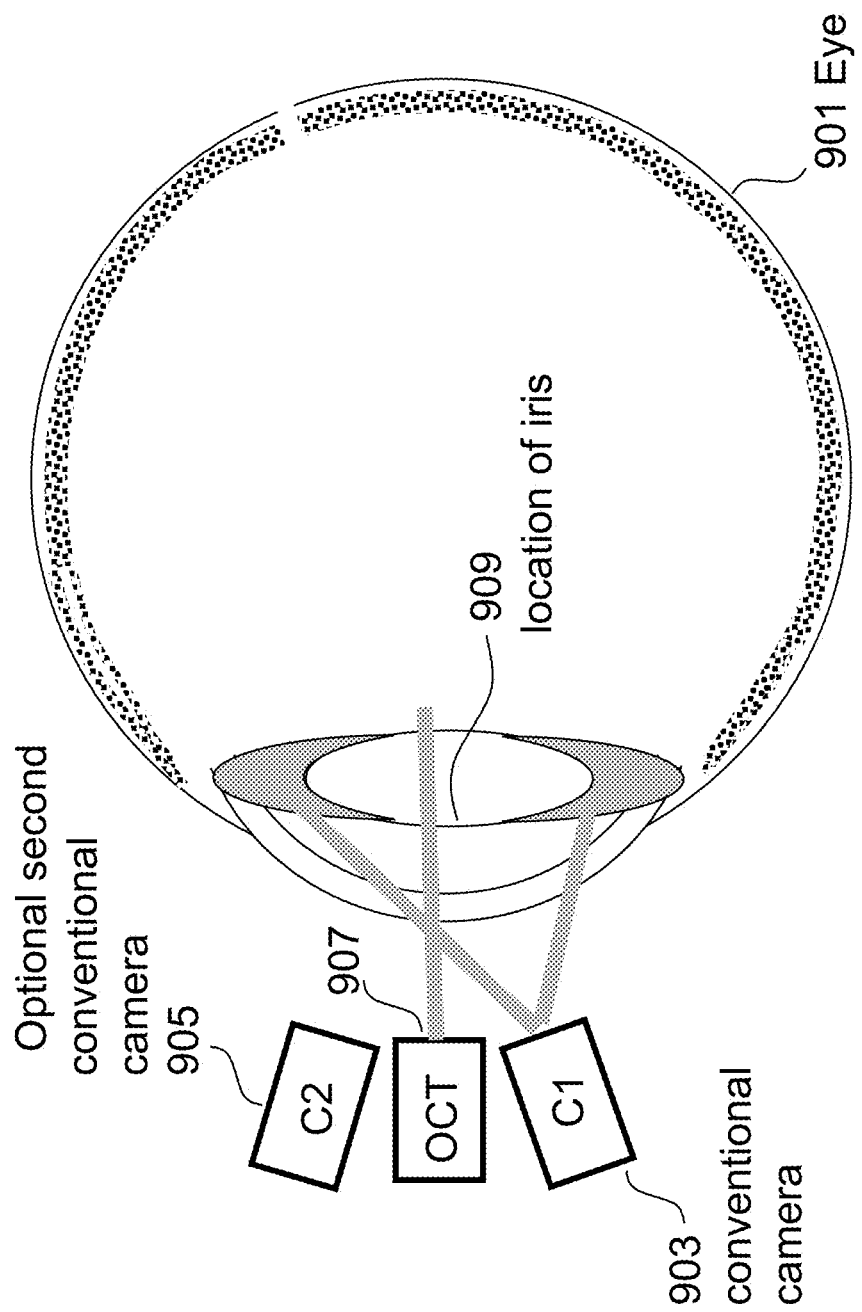
FIG. 9 depicts a conventional camera imaging the iris and an OCT system acquiring a three dimensional and sub-surface image of the iris, and an optional second conventional camera according to an embodiment of the invention.
Figure 10:
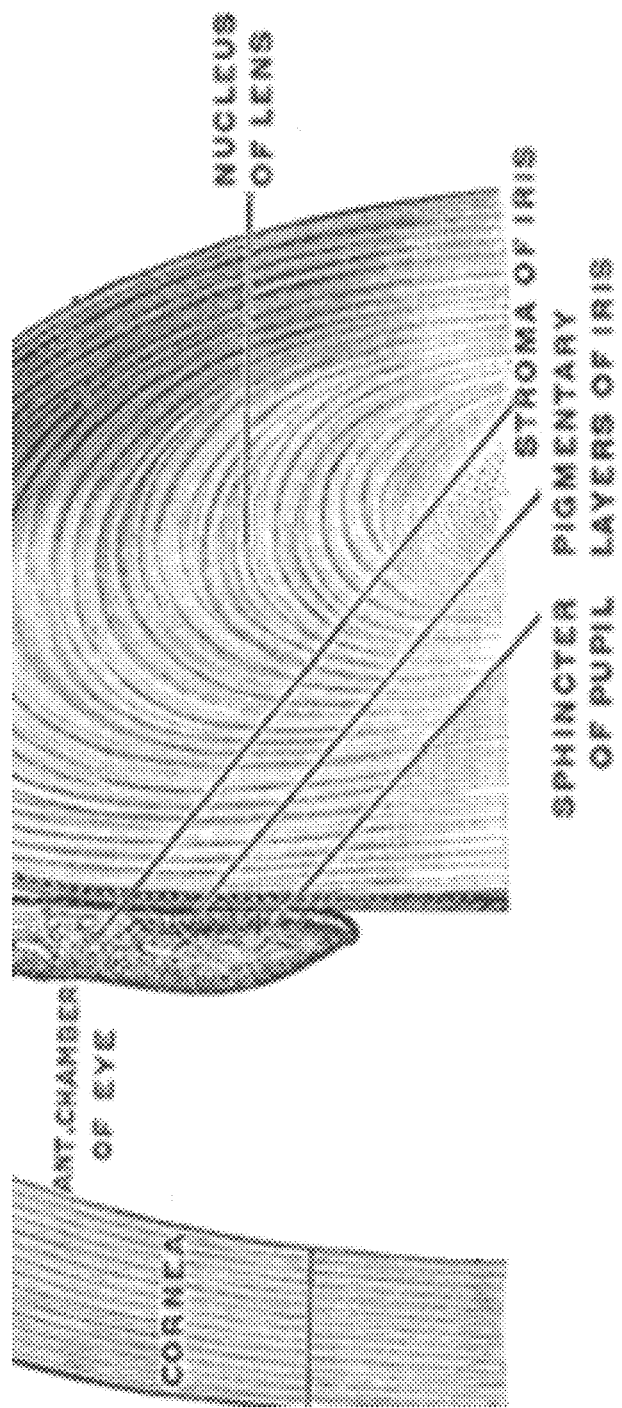
FIG. 10 is sketch of a section of the iris depicting the typical layered structure of the thin posterior epithelium.

Referring now to FIGS. 8 through 10.

FIG. 8, A through B inclusive, shows two views of an iris: FIG. 8A depicts a side view of an iris; FIG. 8B depicts a front view of an iris.

Referring now to FIG. 9, FIG. 9 depicts a conventional camera imaging the iris and an OCT system acquiring a three dimensional and sub-surface image of the iris, and an optional second conventional camera. It can be appreciated that a second camera aids in the positioning of the optical coherent tomography system relative to the surfaces to be imaged. Accordingly, an eye 901 under test and its iris 909, a first conventional camera 903, an optional second conventional camera 905, an OCT 907.

FIG. 10 shows a sketch of a section of the iris depicting the typical layered structure of the thin posterior epithelium and the eye; the cornea; the anterior chamber; the sphincter of the pupil; the pigmentary layers of the iris; the stroma layers of iris; the nucleus of the lens. It can be appreciated that detecting changes in any of these structures relative to incident light exposure provides evidence concerning biointegrity of the structure under test. For example, pupil dilation is verifiable by detecting sphincter muscle contraction.

An embodiment of the invention as depicted in FIG. 9 provides a conventional image of an iris and a three dimensional and subsurface image of the iris. The conventional image of the iris enables establishing the identity of the subject by correlation with a data base. The combination of the conventional image of the iris and the three dimensional and subsurface image of the iris provides an assurance as to the bio-integrity of the structure under test.

In general, with respect to iris recognition, the recognition system can be made more robust by augmenting conventional iris recognition by the use of an OCT system to: (a) detect the presence of an external false iris, such as a contact lens, by monitoring for the sub-surface interface between the back of the contact lens and the front of the cornea and detecting if there is a front surface of the contact lens; (b) detect an iris implant by monitoring the three dimensional structure of the iris and correlating such structure with the conventional 2D iris image; (c) detect the presence of blood in the iris; (d) detect blood flow in the iris; (e) detect blood flow rate in the iris and correlate it with pulse rate; (f) detect and correlate change in blood flow with response to a stimulus.

The OCT system also detects an iris implant by (a) imaging the three dimensional structure of the iris, for example, to verify that the three dimensional front surface structure of the iris is compatible with the iris image captured by the conventional camera, or to verify that the thin posterior epithelium is present on the rear surface of the iris and furthermore to verify that it conforms to the typical layered structure; (b) detecting the presence of the sphincter muscle located by the pupil; (c) detecting the change in shape of sphincter muscle, or the change in shape of other iris structures, as light intensity is varied; and (d) correlating the change in shape of a muscle or other tissue structure or component as light intensity is varied with the change in pupil diameter in response to a light intensity variation.

Such iris tissue structures or components include the circular muscle group referred to as "sphincter pupillae", and a radial muscle group referred to as "dilator pupillae". The sphincter pupillae causes the pupil to contract. The dilator pupillae cause the pupil to dilate when they contract. The OCT system is used to detect and correlate dynamic changes in the sphincter pupillae or the dilator pupillae with dynamic changes in pupil diameter in response to a stimulus, such as a change in light level.

In one embodiment, the light level applied to the eye is repeatedly varied to cause a repetitive variation in the pupil diameter and therefor a repetitive variation in the physical structure of the aforementioned muscles controlling the pupil diameter. The repetitive nature of the dynamic changes in muscle structure, discernable by the imaging capability of the OCT system, facilitates more reliable detection of real iris tissue (as opposed to a fake iris).

Figure 13:
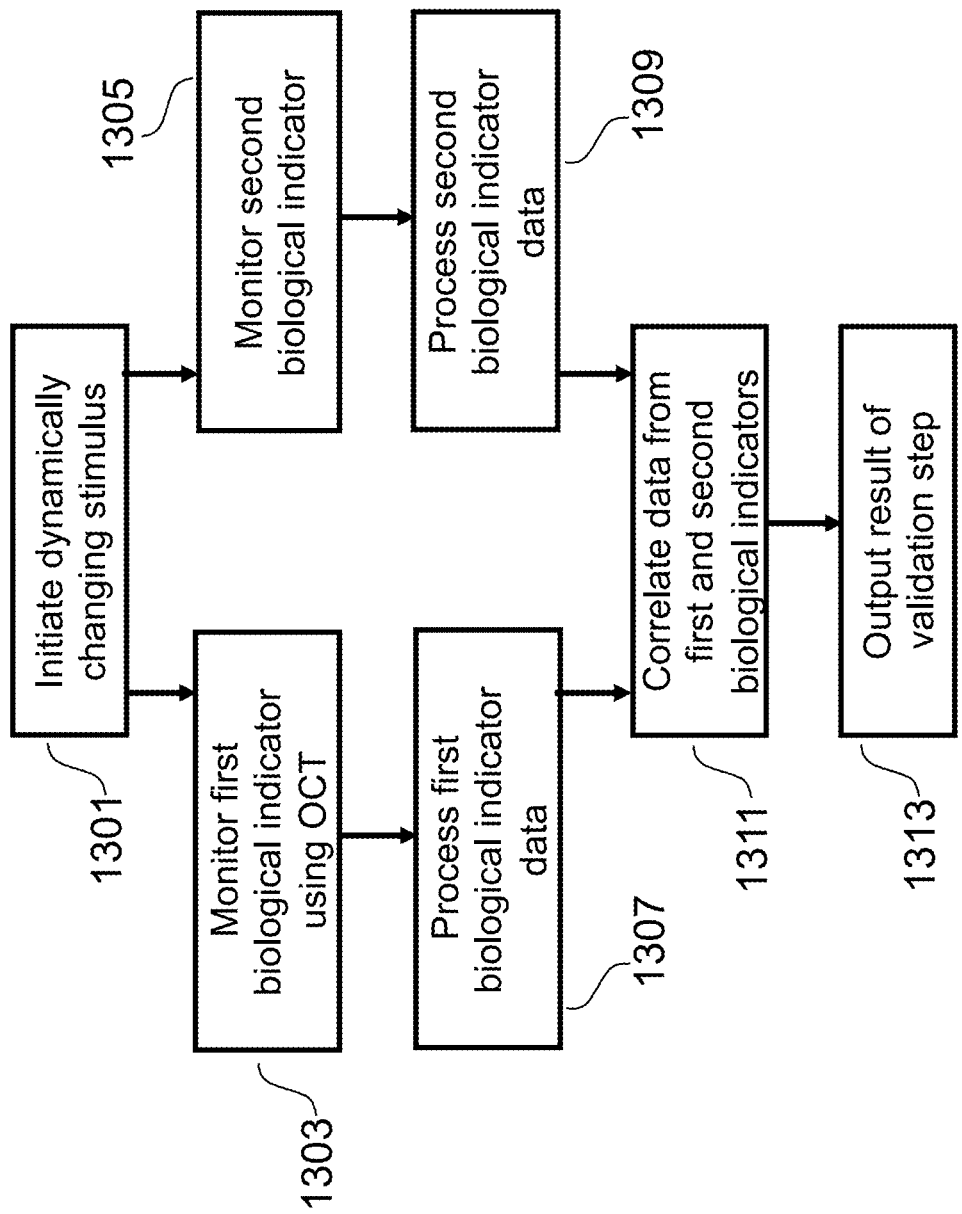
FIG. 13 depicts a method according to the invention.

Referring now to FIG. 13. FIG. 13 depicts one embodiment of the inventive method comprising the steps of: selecting and monitoring at least two biological indicators, exposing subject under test to at least one preselected dynamically changing stimulus; monitoring said at least two biological indicators; processing data obtained during dynamically changing stimulus, and determining whether biological indicators satisfy authenticity criteria. In a preferred embodiment relative to iris recognition, indicators selected are dynamic indicators, including change in pupil diameter and change in sphincter muscle shape, both stimulated by the same change in light level. In facial recognition selected dynamic indicators in a preferred embodiment are blood flow increase or decrease. In fingerprint analysis, selected dynamic indicators are a first and a second pulse blood flow.

While the preferred embodiment involves monitoring at least two biological indicators, other embodiments involve monitoring only one biological indicator. For example in iris recognition, only the (more reliable) dynamic change in a pupil diameter controlling muscle is monitored in response to light level change.

In embodiments where blood flow is a monitored biological indicator, blood flow is monitored by techniques that include, but are not limited to: correlation mapping OCT (cmOCT); nano-scale OCT (nsOCT); and phase sensitive or Doppler OCT.

Referring again to the case of fingerprint recognition, (a) aspects of the sub-dermal structure of tissue under the conventional fingerprint are monitored to verify that it is real living tissue (as opposed to a fake fingerprint) (b) aspects of the sub-dermal fingerprint are correlated with the surface fingerprint to verify that the sub-dermal is consistent with the surface fingerprint (as described in the patent application incorporated herein by reference), (c) physical variation in the size of blood vessels or the speed of blood flow is monitored by the OCT system and correlated with the pulse rate as monitored by conventional pulse rate or heart beat monitors. Furthermore, changes in the physical variation in the size of blood vessels or the speed of blood flow is correlated with changes in the pulse rate or heart beat rate due to an external stimulus, where such a stimulus can be physical or psychological, (d) compression of tissue is monitored by, for example, my measuring the epidermis thickness or the thickness of other layers, and changes in the measured compression are correlated with the changes in the pressure with which the finger applied to the fingerprint platen, where such changes in pressure can be due to the application or removal of the finger from the platen or where an additional sensor monitors the actual pressure of the finger on the platen.

In the case of facial recognition, sub-surface scanning of the surface of the face by the OCT system can be used to verify that the facial tissue has a typical tissue layer structure and is not covered by a mask, for example a liquid latex mask or other disguising make-up. The OCT system can also be used to: detect the presence of blood; blood flow, that the measured blood flow rate varies corresponding with the pulse rate; that a change in blood flow intensity is accompanied by a corresponding change in facial color and/or temperature due, for example, to blushing or blanching in response to stressful questions or stimuli.

OCT measurements acquired by multiple OCT systems or a single OCT system are used to perform multiple measurements. For example an OCT system housed in a goggle like face mounted device makes iris measurements and the OCT beam is routed to make facial measurements. Facial measurements include, for example, monitoring blood flow in the nose.

Other embodiments of a more secure identification and authentication technique include measuring (a) the presence and thickness of a tear film (b) the profile of the tear meniscus at an eye lid margin, referred to as "the tear lake" (c) other parameters of eye including, but not limited to, corneal thickness and curvature, lens thickness, axial length of the eye, (d) mechanical parameters of tissue e.g. how skin deforms and relaxes in response to pressure (e) the polarization changes to light scattered by tissue, for example to determine that linearly polarized light is depolarized and exhibits the birefringence of real tissue (f) the 3D structure of the front of the iris.

Figure 11:
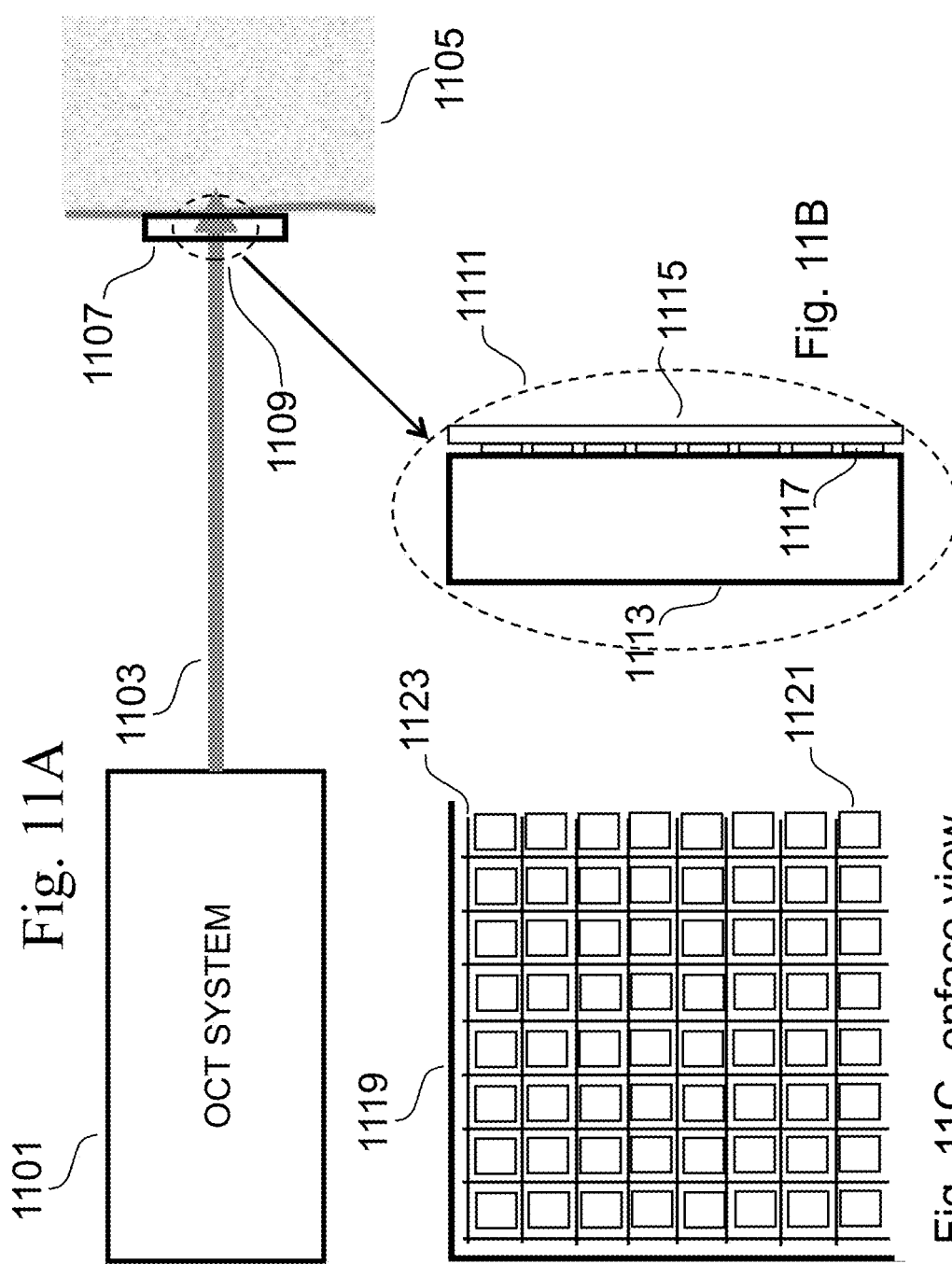
FIGS. 11A, 11B and 11C depicts a combination of an OCT and capacitive array fingerprint imaging system.
Figure 12:
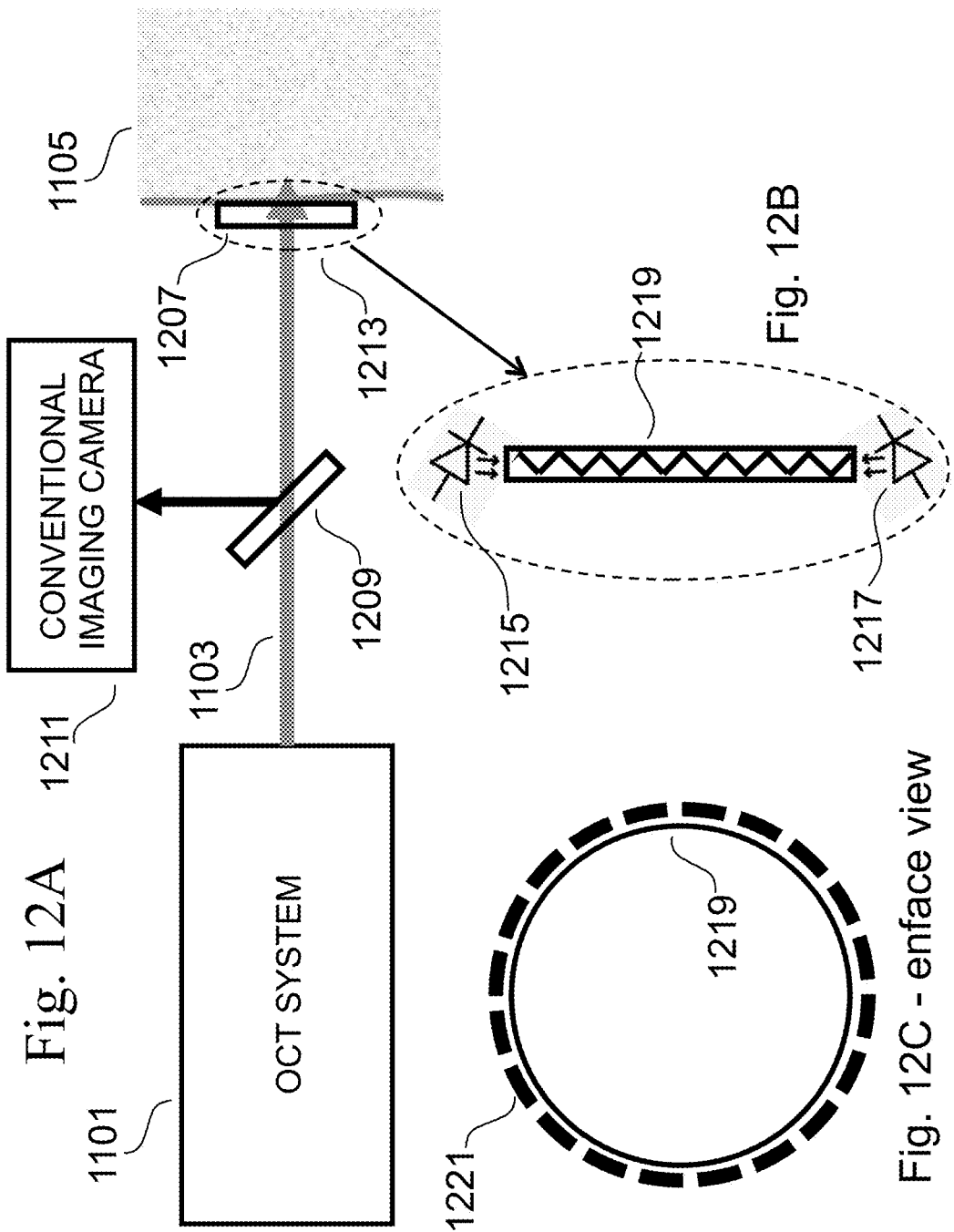
FIGS. 12A, 12B, and 12C depicts a combination of an OCT and a thin FTIR, beam-splitter, and conventional camera based fingerprint imaging system.

Referring again to the case of fingerprint recognition and to FIGS. 11 and 12. An example of an OCT system combined with a surface fingerprint imaging system is illustrated in FIG. 11A of sheet 11. The OCT system 1101 emits a probe beam 1103 that scans the surface of a finger 1105 through a capacitive surface fingerprint imaging system 1107. A section of the capacitive surface fingerprint imaging system 1107 in the small oval 1109 is depicted in more detail in FIG. 11B of sheet 11.

The portion of the capacitive surface fingerprint imaging system 1107 in the oval 1111 depicts a glass substrate layer 1113 and a transparent protective cover layer 1115. Between these two layers is a capacitive array an element of which is indicated by 1117.

A portion of the capacitive array 1119 is depicted as an enface illustration in FIG. 11C of sheet 11. The array consists of a set of transparent capacitive elements, one of which is 1121, comprised of a transparent conductive material, such as indium tin oxide (ITO).

The conductive array, along with horizontal and vertical interconnect lines, one of which is 1123, and the element selecting transistors at the intersections of the interconnect lines are fabricated using transparent thin film technology, including thin film transistors, thereby enabling a completely transparent capacitive sensing array. An example of such a transparent capacitive sensing array is described in a paper titled "Multi Resolution Touch Panel with Built-in Fingerprint Sensing Support" authored by Pranav Koundinya, et al, 2014.

The transparent aspect of the surface fingerprint imaging system, with appropriate anti-reflection coatings, enables the OCT beam to scan through the surface fingerprint imaging system. For optimum OCT imaging the optical path through the surface fingerprint imaging system should also be equal for all perpendicular paths through the surface fingerprint imaging system.

Equal optical path length can be accomplished by using a bonding material to bond the protective layer 1115 to the substrate 1113 and the capacitive array that has a refractive index similar to that of the capacitive array.

Alternatively the capacitive surface fingerprint imaging system can be analyzed by an OCT system to measure and map its optical thickness distribution and the OCT images can then be processed to compensate for any depth offsets.

An alternative combined OCT and surface fingerprint imaging system is illustrated in FIG. 12A of sheet 12 where the surface imager consists of a thin, side illuminated, frustrated total internal reflection (FTIR) element 1207, a beam splitter 1209 and a conventional camera 1211.

The FTIR element 1207 in the small oval 1203 is depicted in greater detail in FIG. 12B of sheet 12 where LEDs 1215 and 1217 illuminate the thin FTIR element 1219 which also depicts the zigzag path of a totally internally reflected light path.

FIG. 12C of sheet 12 depicts one possible implementation of the FTIR element 1219 and an array of LEDs one of which is 1221. An advantage of this embodiment is that LEDs of different wavelengths may be used. Frustrated total internal light of different wavelength beck scattered by the finger tissue can provide different multi-spectral information and information from different penetration depths within the tissue.

Different wavelength LEDs can be powered at different times to enable a single low cost camera to acquire images illuminated by different wavelength at different times.

The LED array can include one or more ultra violet (UV) LEDs that can be used to sterilize the surface of the FTIR element in contact with the finger (also referred to as a platen. UV LEDs or other UV sources can readily be arranged in many alternative configurations to irradiate the platen of many different surface fingerprint capture systems, including, but not limited to, those using FTIR, capacitive arrays or other fingerprint sensing techniques.

It should be understood that the above description is illustrative and not restrictive. Numerous modifications and variations could be made thereto by those skilled in the art without departing from the spirit and scope of the invention. It is therefore to be understood that the invention may be practiced otherwise than as specifically described herein.

The invention claimed is:

1. A system for analyzing an iris in an eye under test comprising:
   an optical coherence tomography system, including a processing system;
   a first conventional camera;
   wherein said first conventional camera monitors dynamic behavior of the pupil of said iris with respect to changing light levels
   and wherein said optical coherence tomography system monitors dynamic behavior of preselected sub-surface components of said iris under test with respect to changing light levels
   and wherein a processing system analyzes dynamic behavior of said pupil and said subsurface components so as to
   determine the correspondence of the conventional camera data and the sub-surface component data and thereby determine the authenticity of said iris under test.

2. The system of claim 1 wherein the sub-surface component of interest is the sphincter of the pupil of said iris, and authenticity is determined by verification of contraction of said sphincter muscle as a consequence of increase in light illumination on said eye.

3. The system of claim 1 wherein said optical coherence tomography system detects the presence of an external false iris by monitoring for the sub-surface interface between the back of the contact lens and the front of the cornea and detecting if there is a front surface of the contact lens.

4. The system of claim 1 wherein said optical coherence tomography system detects an iris implant by monitoring the three dimensional structure of the iris and correlating such structure with the conventional two-dimensional iris image.

5. The system of claim 1 wherein said optical coherence tomography system detect the presence of blood in the iris.

6. The system of claim 1 wherein said optical coherence tomography system detects blood flow in the iris.

7. The system of claim 1 wherein said optical coherence tomography system detects blood flow rate in the iris and correlates said blood flow rate with pulse rate.

8. The system of claim 1 wherein said optical coherence tomography system detects and correlates change in blood flow with response to a stimulus.

* * * * *